US012702512B2

(12) United States Patent
Schneider et al.

(10) Patent No.: US 12,702,512 B2
(45) Date of Patent: Aug. 11, 2026

(54) SURGICAL INSTRUMENT AND STEERING GEAR FOR SAME

(71) Applicant: KARL STORZ SE & CO. KG, Tuttlingen (DE)

(72) Inventors: Janosz Schneider, Donaueschingen (DE); Dominik Längle, Mülheim (DE); Sven Axel Grüner, Trossingen (DE); Jochen Stefan, Wald (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 156 days.

(21) Appl. No.: 18/291,618

(22) PCT Filed: Jul. 25, 2022

(86) PCT No.: PCT/EP2022/070776

§ 371 (c)(1),
(2) Date: Jan. 24, 2024

(87) PCT Pub. No.: WO2023/006655

PCT Pub. Date: Feb. 2, 2023

(65) Prior Publication Data

US 2024/0350217 A1 Oct. 24, 2024

(30) Foreign Application Priority Data

Jul. 28, 2021 (DE) ..................... 10 2021 119 522.5

(51) Int. Cl.
*A61B 34/00* (2016.01)
*B25J 9/10* (2006.01)
(Continued)

(52) U.S. Cl.
CPC ............... *A61B 34/71* (2016.02); *B25J 9/104* (2013.01); *B25J 9/126* (2013.01); *A61B 2034/301* (2016.02)

(58) Field of Classification Search
None
See application file for complete search history.

(56) References Cited

U.S. PATENT DOCUMENTS 5,454,827 A 10/1995 Aust et al.
5,649,956 A * 7/1997 Jensen ..................... B25J 18/04 606/1

(Continued)

FOREIGN PATENT DOCUMENTS

CA 345319 A 10/1934
CN 103552088 A 2/2014

(Continued)

OTHER PUBLICATIONS

International Preliminary Report on Patentability, Application No. PCT/EP2022/070776, mailed Jan. 18, 2024. ISA/European Patent Office.

(Continued)

*Primary Examiner* — Shirley X Jian
(74) *Attorney, Agent, or Firm* — Brooks Kushman P.C

(57) ABSTRACT

A steering gear for a surgical instrument having a shaft and an angling mechanism at the distal end of the shaft, includes two motorised drives and is designed to spatially adjust a wobble plate via the adjustment angle of the two drives. The two drives each have a drive wheel driven designed as a double wheel with a bevel wheel rim and a drive rim. The wobble plate is arranged between the two drive wheels, which have a common axis of rotation, and the drive rims of both double wheels are operatively connected to a respective pinion. The pinions can be driven by the respective motor via a respective driveshaft, wherein the two drive axes run parallel to one another and parallel to the common axis of (Continued)

rotation of the two drive wheels. The invention also relates to a surgical instrument comprising a steering gear of this type.

15 Claims, 7 Drawing Sheets

(51) Int. Cl.
*B25J 9/12* (2006.01)
*A61B 34/30* (2016.01)

(56) References Cited

U.S. PATENT DOCUMENTS

| | | | | |
|---|---|---|---|---|
| 6,331,181 | B1 * | 12/2001 | Tierney | G16H 40/63 606/130 |
| 7,699,855 | B2 | 4/2010 | Anderson et al. | |
| 10,105,128 | B2 | 10/2018 | Cooper et al. | |
| 11,660,155 | B2 * | 5/2023 | Grüner | A61B 17/29 606/130 |
| 12,396,744 | B2 * | 8/2025 | Stefan | A61B 17/29 |
| 12,539,185 | B2 * | 2/2026 | Grüner | A61B 17/29 |
| 12,558,114 | B2 * | 2/2026 | Schneider | A61B 17/29 |
| 2008/0287963 | A1 * | 11/2008 | Rogers | A61B 1/008 606/130 |
| 2010/0228284 | A1 | 9/2010 | Cooper et al. | |
| 2015/0352728 | A1 * | 12/2015 | Wang | B25J 18/06 74/490.04 |
| 2016/0066982 | A1 | 3/2016 | Marczyk et al. | |
| 2021/0018241 | A1 | 1/2021 | Zhang et al. | |
| 2021/0038331 | A1 * | 2/2021 | Grüner | B25J 9/1035 |
| 2023/0030616 | A1 * | 2/2023 | Grüner | A61B 17/00234 |
| 2024/0350159 | A1 * | 10/2024 | Stefan | A61B 34/71 |
| 2024/0350217 | A1 * | 10/2024 | Schneider | A61B 17/29 |
| 2024/0423738 | A1 * | 12/2024 | Grüner | A61B 17/29 |
| 2025/0009376 | A1 * | 1/2025 | Schneider | A61B 17/29 |

FOREIGN PATENT DOCUMENTS

| | | | |
|---|---|---|---|
| CN | 109866335 | A | 6/2019 |
| CN | 112315409 | A | 2/2021 |
| DE | 102019121092 | A1 | 2/2021 |
| WO | 2014004242 | A1 | 1/2014 |

OTHER PUBLICATIONS

International Search Report, Application No. PCT/EP2022/070776, mailed Oct. 26, 2022. ISA/European Patent Office.

China State Intellectual Property Office, Search Report issued for Application No. 2022800518969, dated May 26, 2026.

* cited by examiner 13
17‘
C‘
C
16b
19.2
15b
17
15a
16a
19‘
3
19.1
18‘
12
22
18.1
B, A
2

SURGICAL INSTRUMENT AND STEERING GEAR FOR SAME

CROSS-REFERENCE TO RELATED APPLICATIONS

This application is the U.S. national stage of PCT/EP2022/070776 filed on Jul. 25, 2022, which claims priority of German Patent Application No. 10 2021 119 522.5 filed on Jul. 28, 2021, the contents of which are incorporated herein.

TECHNICAL FIELD

The disclosure relates to a surgical instrument and a steering gear for same.

BACKGROUND

From the prior art, surgical instruments are known which can be guided manually or by a robot and which have tools whose tool tip can be pivoted by means of a plurality of pivot members engaging in one another. These pivot members are connected to a multiplicity of steering wires or steering cables in order to achieve delicate control of the tool tip. A more uniform force distribution in all deflection directions can be obtained by way of a plurality of thin steering wires in comparison with a few thicker steering wires.

For example, a generic surgical instrument is known from U.S. Pat. No. 5,454,827, in which the distal-side pivot members are coupled via four steering wires to a spatially adjustable wobble plate arranged on the proximal side, in such a way that a movement of the spatially adjustable wobble plate causes a corresponding relative movement of the distal-side pivot members and hence a pivoting of the tool tip, with the movement of the spatially adjustable wobble plate being implemented manually by way of a type of joystick that is directly coupled therewith.

The design of the drive for the steering wires with the spatially adjustable wobble plate, on which all four steering wires are mounted, is advantageous in that this enables a spatially compact structure and only requires the movement of one component to be able to address all steering wires.

Disadvantages of this known structure include the use of only a small number of steering wires, specifically only four steering wires, and also the purely manual manipulability of the spatially adjustable plate serving as the drive for the steering wires, whereby a sensitive and reproducible adjustment of the distal-side pivot members is hardly possible.

U.S. Pat. No. 7,699,855 has disclosed a surgical instrument having an interface that enables the connection of the instrument to a robotic arm. In this case, all drives controlling the instrument are arranged in the robotic arm. The transfer of the rotary angles from drives to the instrument is implemented by way of coupling plates in a common separation plane, and so the drive axes are parallel to one another and perpendicular to this plane.

WO 2014/004242 also describes such an interface, wherein the axially parallel drives are also installed in the robotic arm in this case.

The aforementioned design is linked to a complex structure and an indirect control afflicted with play because the drives are not arranged directly in the surgical instrument. The resultant nonlinear transmission behavior of the drive movement to the wobble plate moreover can only be mapped poorly in a software control.

U.S. Pat. No. 10,105,128 B2 also discloses a control of such a tool tip; in that case, this is implemented by way of a mechanism comprising toothed lock washer segments and joint rods for transmitting the movement of the drives to the wobble plate.

SUMMARY

Proceeding from this prior art, it is an object of the present disclosure to provide an improved steering gear for a surgical instrument which has a drive of the spatially adjustable wobble plate with linear transmission behavior.

This object is achieved by a steering gear having the features of claim 1.

The further object of providing a surgical instrument whose spatially adjustable wobble plate is driven by a structurally simple and space-saving steering gear is achieved by the surgical instrument having the features of independent claim 8.

Developments and preferred embodiments of the steering gear and the surgical instrument are defined in the dependent claims.

According to a first embodiment of the steering gear according to the disclosure for a surgical instrument, wherein the steering gear is arrangeable at the proximal end of a hollow shaft which defines a longitudinal axis B of the instrument and, at the distal end, comprises a deflection mechanism of the surgical instrument, it comprises two motorized drives and is designed to spatially align a wobble plate by way of the adjustment angles of the two drives. In turn, the wobble plate is designed to control the distal deflection mechanism of the surgical instrument.

According to the disclosure, the first drive comprises a first drive wheel which is driven by a first motor and designed as a double wheel with a first bevel gear rim and a first drive rim. The second drive also comprises a second drive wheel which is driven by a second motor and designed as a double wheel with a second bevel gear rim and a second drive rim. The wobble plate is arranged between the two drive wheels, which have a common axis of rotation A, wherein the bevel gear rims are arranged facing one another. The drive rims of both double wheels are operatively connected to a respective pinion, wherein a first pinion which is operatively connected to the first drive rim is drivable by the first motor via a first drive shaft, which defines a first drive axis C. A second pinion which is operatively connected to the second drive rim is drivable by the second motor via a second drive shaft, which defines a second drive axis C'. In this case, the two drive axes C, C' run parallel to one another and parallel to the common axis of rotation A of the two drive wheels, and so the drive axes can be positioned close to the longitudinal axis B of the instrument, saving installation space in the process.

As a result of the motorized drive of the spatially adjustable plate by means of the steering gear, which has a linear transmission behavior with the driven double wheels, it is possible to activate the distal-side tool tip precisely, delicately in very small increments, and also reproducibly. In this case, the double wheels may optionally be formed in one piece; however, it is also possible for each double wheel to consist of a bevel gear and a drive wheel, which are connected to one another. The combination of drive wheel rim and bevel gear rim brings about a direct transmission of the movements initiated by the drives to the wobble plate.

In an embodiment of the steering gear according to the disclosure, the two double wheels can be arranged relative to the wobble plate in such a way that the two drive axes C, C' and the common axis of rotation A of the two double wheels run perpendicular, which is to say at right angles, to the longitudinal axis B of the surgical instrument. In space-saving fashion, both motors can be arranged next to one another on one side in relation to the longitudinal axis B, perpendicular thereto, with the result that the installation height can be reduced. Depending on installation space available, however, an arrangement of the two motors diametrically offset from one another in relation to the longitudinal axis B is also conceivable.

In an alternative embodiment of the steering gear according to the disclosure, the two drive wheels can be designed as hollow double wheels and be arranged relative to the wobble plate in such a way that the common axis of rotation A of the two hollow double wheels is flush, or coincides, with the longitudinal axis B of the surgical instrument, and the two drive axes C, C' run parallel to the longitudinal axis B of the surgical instrument. This also enables an installation space-saving arrangement of the motors near the longitudinal axis—to be precise, in parallel therewith.

It is possible in both arrangement variants of the steering gear for the drive rims of the double wheels or hollow double wheels to be gear rims and for the pinions to accordingly be gear wheels, which directly engage or mesh with the drive rims designed as gear rims.

As an alternative to the operative connection of gear rim and gear wheel, a further embodiment provides for the drive rims of the double wheels or hollow double wheels and the pinions to be respectively designed as pulleys with an all-around profile for a drive belt, wherein a first drive belt provides the operative connection between the first drive rim and the first pinion and a second drive belt enables the operative connection between the second drive rim and the second pinion.

Flat belts, round belts, V-belts, ribbed V-belts, or toothed belts can be chosen as drive belts, wherein the all-round profile of the drive rims designed as pulleys and the pinions accordingly is a flat profile, round profile, V-profile, ribbed V-profile or toothed profile. Toothed belts may be preferable since the interlock between toothed belt and toothed profile at the pulleys not only allows high forces to be transmitted with a lower pretension but especially also prevents slippage, and thus ensures an exact control.

In the case of a chain drive as an alternative to the belt drive, the drive rims of the double wheels or hollow double wheels and the pinions are accordingly designed as sprockets for a drive chain, wherein a first drive chain provides the operative connection between the first drive rim and the first pinion and a second drive chain provides the operative connection between the second drive rim and the second pinion. A belt drive may be preferred over a chain drive on account of the lower costs and smoother operation.

Additionally, for controlling the wobble plate, a further embodiment according to the disclosure of the steering gear may provide for the wobble plate to be coupled to a third gear wheel which meshes with the two bevel gear rims of the two double wheels or hollow double wheels and whose axis of rotation D is at right angles to the common axis A of the double wheels. In this way, the adjustment movements of the drives can be transferred via the (hollow) double wheels to the third gear wheel and, from the latter, to the wobble plate, which can thereby be tilted or pivoted about the two axes of rotation A and D. Preferably, the wobble plate can also be coupled to a fourth gear wheel which is coupled to the two bevel gear rims of the two double wheels or hollow double wheels and arranged on the side facing away from the third gear wheel on its axis of rotation D.

The disclosure also relates to a surgical instrument. According to the first embodiment of the surgical instrument, the latter comprises a shaft, a manipulation unit arranged at the proximal end of the shaft, and a tool arranged at the distal end of the shaft. The tool comprises a tool tip which can be deflected by means of a distal deflection mechanism. The deflection mechanism can be controlled or aligned by means of a wobble plate that is spatially alignable by means of two drives, for the purposes of which the surgical instrument comprises a steering gear according to the disclosure, wherein the two drives are part of the steering gear according to the disclosure, which is designed to transfer the adjustment angles of the two drives to the spatial alignment of the wobble plate in order thus to control the deflection mechanism.

As a result of the steering gear according to the disclosure, the surgical instrument can be constructed in structurally simple and space-saving fashion, with the result that a simple connection to a robotic arm can be enabled, in the case of which the movement of the drives can be transmitted linearly to the tool tip. The consequence is a precisely controllable use of the surgical instrument.

To be able to three-dimensionally adjust the spatially adjustable wobble plate despite the coupling for conjoint rotation with the third gear wheel which meshes with the two bevel gear rims of both double wheels, which is to say to be able to overlay the tilt or pivot movements with a rotation of the wobble plate about the longitudinal axis B, a preferred embodiment of the surgical instrument can provide for the wobble plate, via a bearing ring, to be mounted so as to be rotatable about the longitudinal axis B of the shaft in a steering ring that is coupled for conjoint rotation with the third gear wheel. For the rotative coupling of the wobble plate with a main shaft running coaxially to a longitudinal axis B of the shaft, the wobble plate can be gimbal-coupled with the main shaft. Hence, the tool tip can be rotated about the longitudinal axis of the shaft by means of the wobble plate, in addition to the pivoting or tilting relative to the longitudinal axis of the shaft by way of the two drives and by way of the main shaft.

To form the gimbal mount of the spatially adjustable wobble plate, an embodiment of the surgical instrument according to the disclosure may provide for the wobble plate to be pivotably mounted on a universal joint plate by way of two bearing pins arranged offset from one another by 180°, wherein the universal joint plate is pivotably mounted on the main shaft by way of two bearing pins arranged offset from one another by 180°, and wherein the bearing pins of the wobble plate and the universal joint plate are arranged offset from one another by 90°. The gimbal suspension enables a movement guidance in all three spatial axes, whereby the tool tip can be controlled in targeted fashion. As an alternative to a universal joint plate with two pin pairs crossed at right angles for the gimbal mount of the wobble plate on the main shaft, an advantageous embodiment may, for gimbal mounting purposes, provide for the main shaft to comprise two guide grooves present in its outer face, said guide grooves extending diametrically and along the main shaft, wherein the wobble plate, which has an annular embodiment with an outer side and an inner side, comprises two diametrically and radially inwardly pointing pins arranged on the wobble plate. Each one of the two pins securely assembled on or in the wobble plate engages in one of the guide grooves introduced into the main shaft on both sides, with the result that a rotary angle of the shaft is transferable to the wobble plate. Advantageously, this yields a rotationally rigid connection between the main shaft and wobble plate, which allows a rotary angle transfer even in the case of a large angle offset (+40° and more) and axial offset, and which in the process has a very compact design, and is simple to produce and assemble. However, for the gimbal mount of a wobble plate on a main shaft, use could in principle also be made of a curved tooth coupling despite a relatively small angular offset, a constant velocity joint despite the complicated fabrication and complex assembly, or an integrally bonded coupling, which is frequently linked to a play-afflicted rotary angle transfer.

In a further embodiment of the surgical instrument according to the disclosure, steering wires connected to the wobble plate of the steering gear run in the longitudinal direction of the shaft. Preferably, the steering wires may be detachably fastened to the wobble plate, for example by means of a clamping connection, so that, in the case of damage, the steering wires can easily be replaced. The wobble plate being rotationally coupled to the main shaft and being rotatably mounted in the steering ring as a result of the bearing ring, said steering ring being coupled for conjoint rotation with the third gear wheel, further advantageously prevents twisting of the steering wires when pivoting the tool tip relative to the longitudinal axis and when performing a rotation about the longitudinal axis of the shaft.

Also, an even further embodiment of the surgical instrument according to the disclosure provides for the fourth gear wheel to be coupled to the wobble plate via a bearing ring with the steering ring, wherein the fourth gear wheel is freely rotatable vis-à-vis the third gear wheel. This fourth gear wheel closes the all-round toothing chain and thus ensures a uniformly all-around and play-free force distribution.

In a further embodiment of the surgical instrument according to the disclosure, a manipulation element is axially displaceably mounted in the shaft (and the main shaft) and is operatively connected on the proximal side to the manipulation unit. The distal deflection mechanism of the tool tip able to be deflected consists of pivot members which are arranged at the distal end of the shaft and are connected to the wobble plate via the steering wires running in the longitudinal direction of the shaft.

In a further embodiment of the surgical instrument according to the disclosure, a radial distance of the steering wires from the longitudinal axis of the shaft is greater at the wobble plate than at the proximal end of the shaft, from where the steering wires emerge. In this case, the steering wires may extend directly to the wobble plate from the proximal end of the shaft, with the steering wires running at an angle with respect to the wobble plate that deviates from 90°. Alternatively, a fan plate can be arranged on the main shaft distally in front of the wobble plate, said fan plate increasing the radial distance of the steering wires, which emerge from the proximal shaft end, from the longitudinal axis of the shaft such that the steering wires run approximately parallel to one another between the fan plate and the wobble plate and, in relation to a plate surface of the wobble plate, form an angle of approx. 90°. The variant without fan plate may be preferred on account of the smaller installation space requirements. As a result of increasing the radial distance of the steering wires from the longitudinal axis of the shaft, for example from a diameter of 4 mm to a diameter of 18 mm, it is not only the assembly and fabrication of the drive of the steering wires which is equipped with the spatially adjustable plate that is simplified, but also the adjustment angle of the spatially adjustable plate or, as a consequence of the increased lever, the forces required for deflection that is/are reduced, which is done in order to obtain a pivot angle of the tool tip that corresponds to the extent of the diameter increase.

Cutouts for the steering wires and the manipulation element may be formed in the gear rims of the third gear wheel and fourth gear wheel in order to avoid a collision of the gear wheels with the steering wires and optionally with the manipulation element when the third and fourth gear wheel are pivoted relative to the longitudinal axis of the shaft.

The surgical instrument according to the disclosure is advantageous in that many thin steering wires can be used to control the pivotable tool tip and that, on account of the motorized drive for the spatially adjustable plate on which the steering wires are mounted proximally, this control is sensitive, precise and reproducible.

Further embodiments, and some of the advantages associated with these and with further embodiments, are made clear and more understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description, and the claims contain numerous features in combination. A person skilled in the art will expediently also consider the features on an individual basis and combine them to form further advantageous combinations.

DETAILED DESCRIPTION OF PREFERRED EMBODIMENTS

Figure 1:
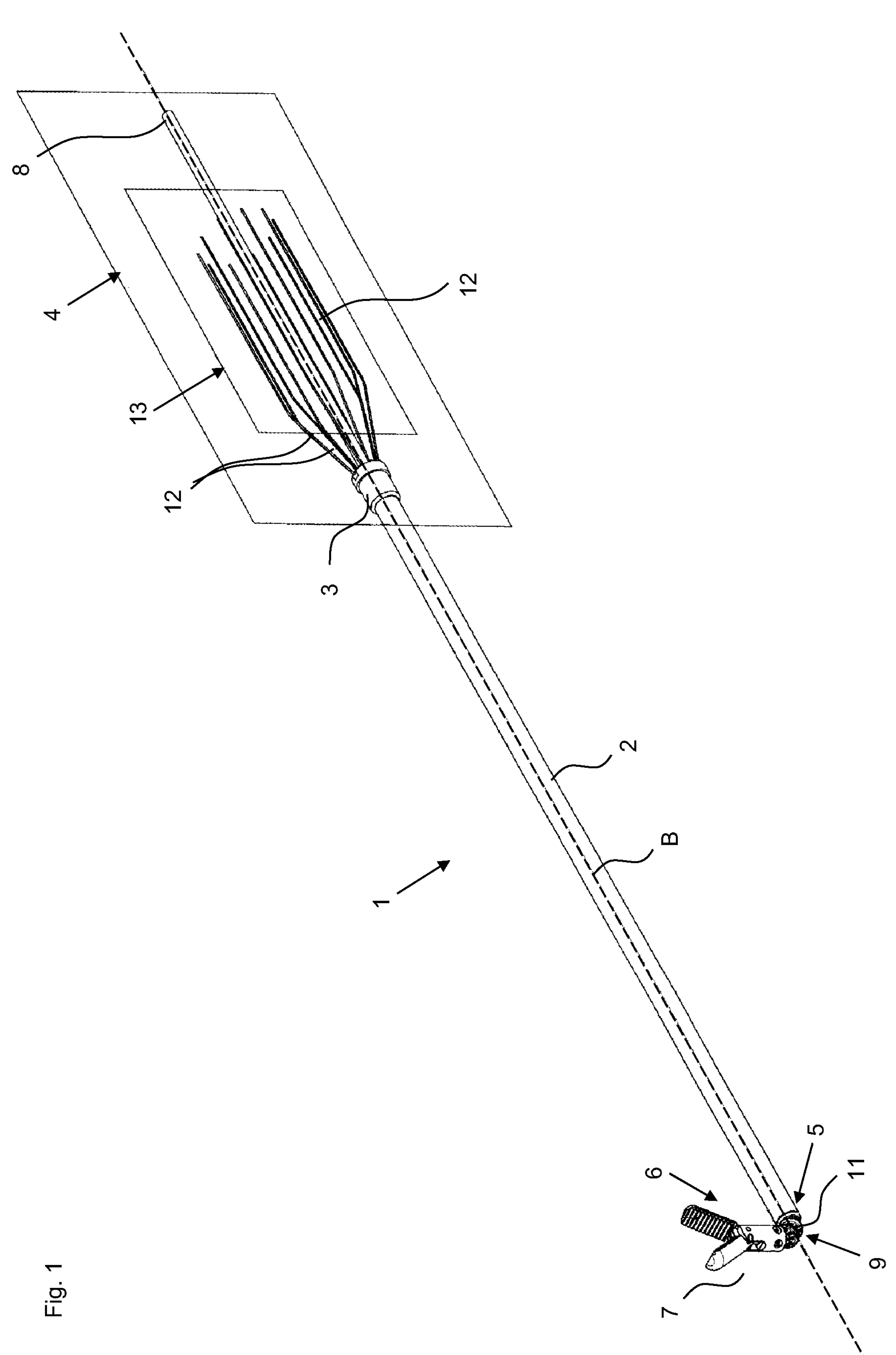
FIG. 1 shows a schematic perspective side view of a medical instrument according to the disclosure.

FIG. 1 shows a surgical instrument 1 with a hollow shaft 2 which comprises an only schematically depicted manipulation unit 4 arranged at the proximal end 3 of the shaft 2 and a tool tip 6 arranged at the distal end 5 of the shaft 2. The tool tip 6 is connected to an instrument 7 which is manipulable by way of a manipulation element 8 which is axially displaceably mounted in the shaft 2 and, on the proximal side, operatively connected to the manipulation unit 4. The manipulation unit 4 can be a manually manipulable handle, or else an assembly designed for robotic use, which is to say an assembly that is manipulable without manual assistance as well.

For example, the instrument 7 of the tool tip 6 can be a tool provided with jaws, as depicted in FIG. 1, or else an endoscope, an applicator, or the like.

The tool tip 6 is pivotable relative to the longitudinal axis 10 of the shaft 2 by way of a hinge mechanism 9, wherein the hinge mechanism 9 consists of pivot members 11 which are arranged at the distal end of the shaft 5 and connected via steering wires 12 running in the longitudinal direction B of the shaft 2 to a drive or steering gear 13 arranged at the proximal end 3 of the shaft 2, in such a way that a movement of the proximal-side steering gear 13 causes a corresponding relative movement of the distal-side pivot members 11 and hence a pivoting of the tool tip 6.

Even though exclusive use is made of the term steering wires 12 hereinabove and below, from a functional point of view use can also be made of steering cables, which is why the used term steering wires 12 should also be read and understood synonymously as steering cables.

The axially displaceable manipulation element 8, which is mounted in the shaft 2 and serves to manipulate the instrument 7 for example consisting of two jaw parts, is in the form of a push/pull rod in the embodiments depicted.

In the medical instrument 1 depicted in the drawings and described below, the steering gear 13 for the steering wires 12 is in the form of a motorized drive 13.

In yet a further embodiment of the surgical instrument according to the disclosure, the wobble plate is mounted in a steering ring so as to be rotatable about the longitudinal axis B of the shaft. To this end, a bearing ring coupled for conjoint rotation with the third gear wheel is provided in the steering ring. This serves to also allow the tool tip to be rotated about the longitudinal axis of the shaft, in addition to the pivoting relative to the longitudinal axis of the shaft, without the steering wires becoming twisted.

The core of the drive 13 is a spatially adjustable plate or wobble plate 14 (FIGS. 3, 9, 10), on which the steering wires 12 are mounted such that a displacement of the wobble plate 14 causes a pivoting of the tool tip 6 by way of the steering wires 12 mounted on the wobble plate 14. The wobble plate 14 can be displaced by means of the motorized drive or steering gear 13.

By using a motorized drive 13 for the wobble plate 14, it is possible to control the steering wires 12 for pivoting the distal-side pivot members 11 or the tool tip 6 precisely, sensitively in very small increments, and also in reproducible fashion. Moreover, the number of steering wires 12 to be used for a motorized drive 13 can be chosen quite freely.

As shown in FIGS. 2 to 9, the steering gear 13 comprises two drives with motors 17, 17' (not depicted in FIG. 9) with parallel drive axes C, C', which also run parallel to a common axis of rotation A of the two drive wheels 18, 19, between which the spatially adjustable wobble plate 14 is arranged.

Figure 2:
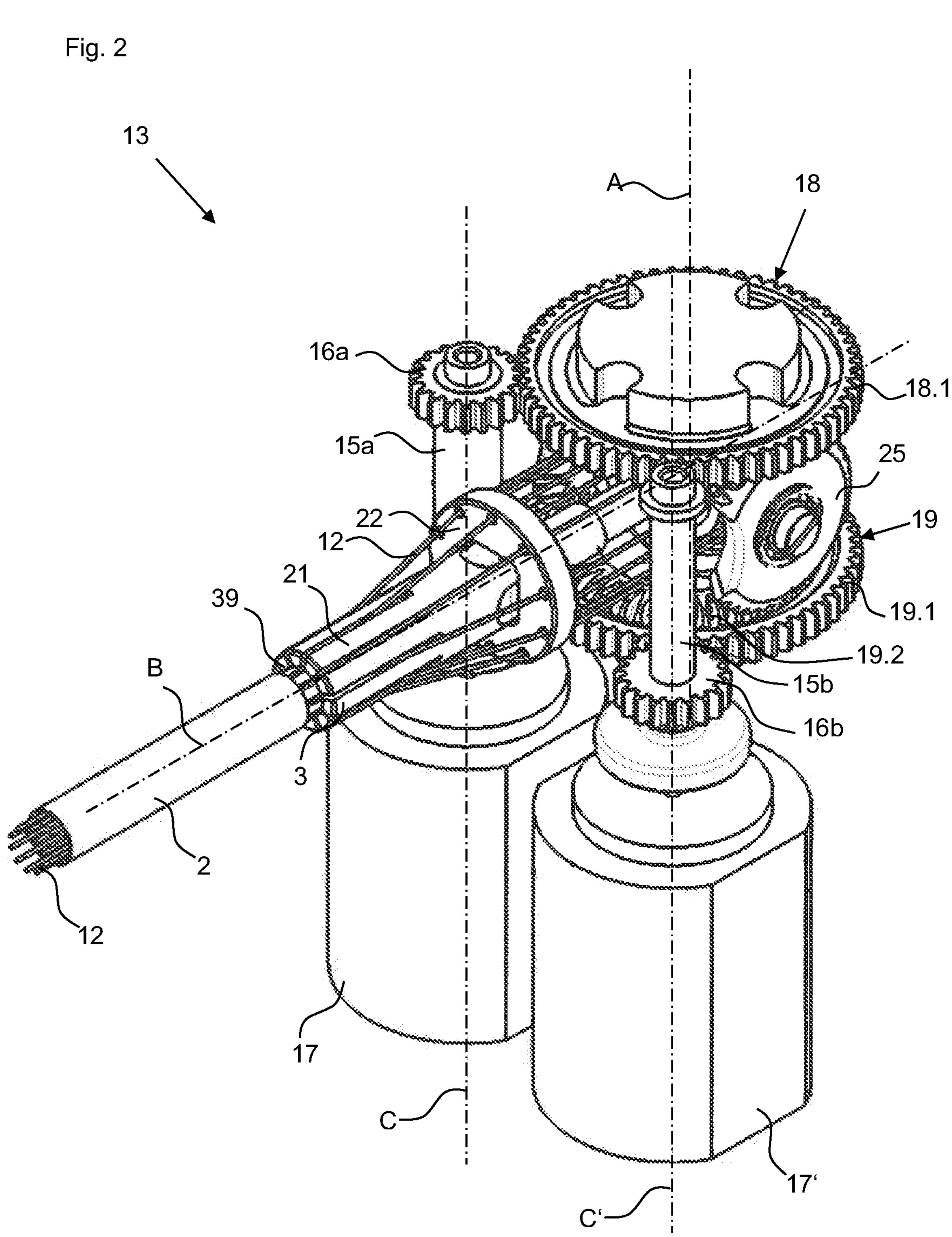
FIG. 2 shows a perspective view of the drive according to FIG. 1 in a first embodiment.
Figure 3:
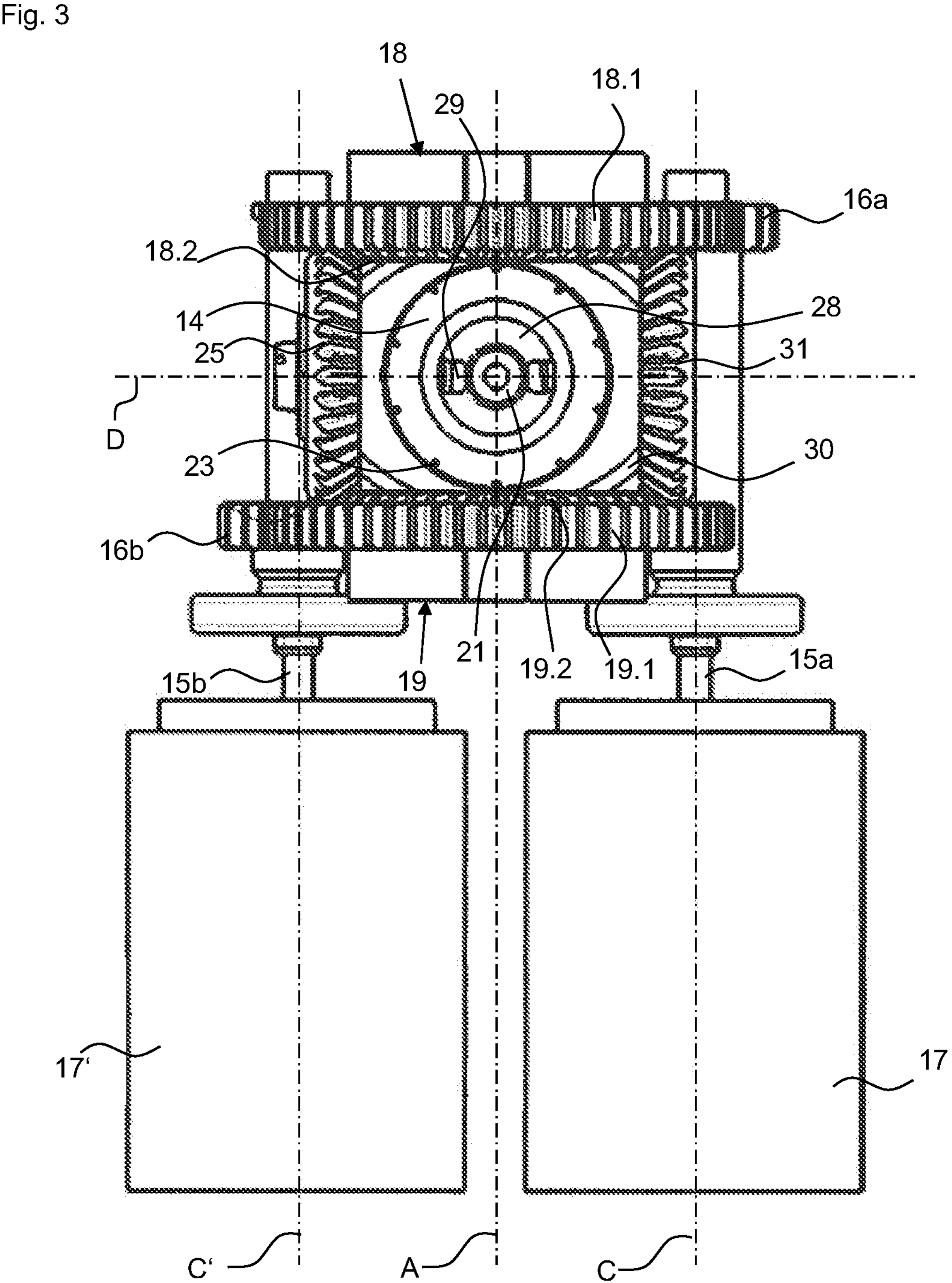
FIG. 3 shows a rear view of the drive according to FIG. 2.

FIGS. 2 and 3 show an example of a first embodiment of the steering gear 13 according to the disclosure for a surgical instrument 1 which, as shown in FIG. 1, is arranged at the proximal end 3 of the shaft 2 which defines the longitudinal or main axis B and comprises the deflection mechanism 9 at the distal end 5. The drives of the steering gear 13 comprise a first drive wheel 18 driven by the first motor 17 and a second drive wheel 19 driven by the second motor 17', between which the wobble plate 14 is arranged. The two drive wheels 18, 19 are located on a common axis of rotation A and are both designed as double wheels 18, 19, and so they each comprise a bevel gear rim 18.2, 19.2 and a drive rim 18.1, 19.1. The double wheels 18, 19 can preferably be manufactured in one piece. However, it is alternatively likewise possible for each double wheel to respectively consist of a bevel gear and a wheel with a drive rim connected thereto.

The bevel gear rims 18.2, 19.2 of the double wheels 18, 19 face one another and mesh with a third gear wheel 25 and, arranged opposite to the latter, a fourth gear wheel 31, said gear wheels being coupled to the wobble plate 14 and being located on an axis of rotation D that is at right angles to the common axis A of the double wheels 18, 19.

To transmit the adjustment movements of the motors 17, 17' to the drive wheels 18, 19, the steering gear 13 comprises a first pinion 16*a*, which is driven via a first drive shaft 15*a* by the first motor 17 and meshes with the drive rim 18.1 of the first double wheel 18. Accordingly, the second pinion 16*b*, which meshes with the drive rim 19.1 of the second double wheel 19, is driven via a second drive shaft 15*b* by the second motor 17'. The drive shafts 15*a* and 15*b* define the first and second drive axis C and C', which not only run parallel to one another but also parallel to the common axis of rotation A of the two drive wheels 18, 19.

By way of this arrangement, the two driven double wheels 18, 19 of the steering gear 13 can be arranged relative to the wobble plate 14 in such a way that the two drive axes C, C' and the common axis of rotation A of the two double wheels 18, 19 run perpendicular, which is to say at right angles, to the longitudinal axis B of the surgical instrument 1. In this way, the drive axes C, C' can be positioned relatively close to the longitudinal axis B. Since the upshot of the steering gear 13 is that the motors 17, 17' need not be installed opposite one another in order to move the two drive wheels 18, 19, the installation height of the instrument can be reduced by the parallel arrangement of the two motors 17, 17' next to one another on one side in relation to the longitudinal axis B.

Figure 4:
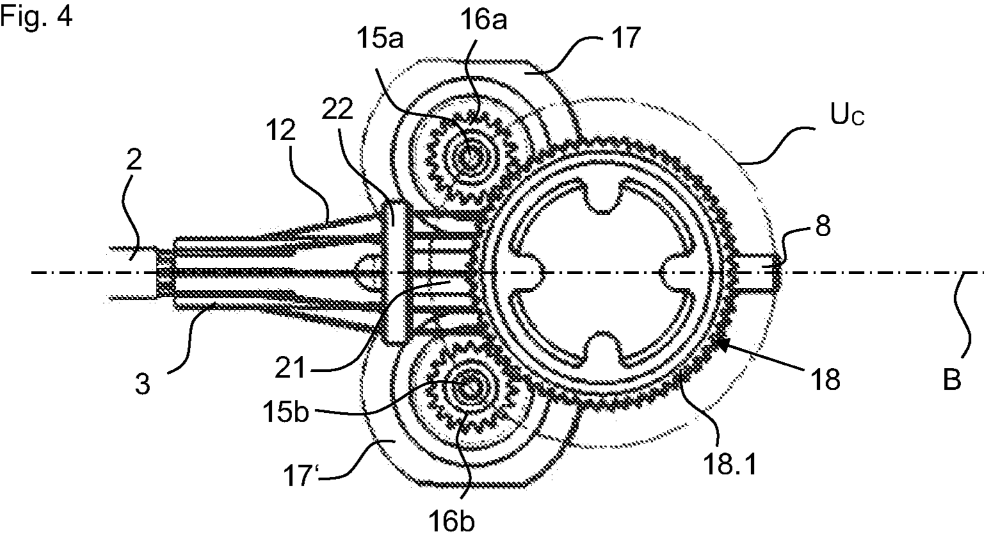
FIG. 4 shows a plan view of the drive according to FIG. 2.
Figure 5:
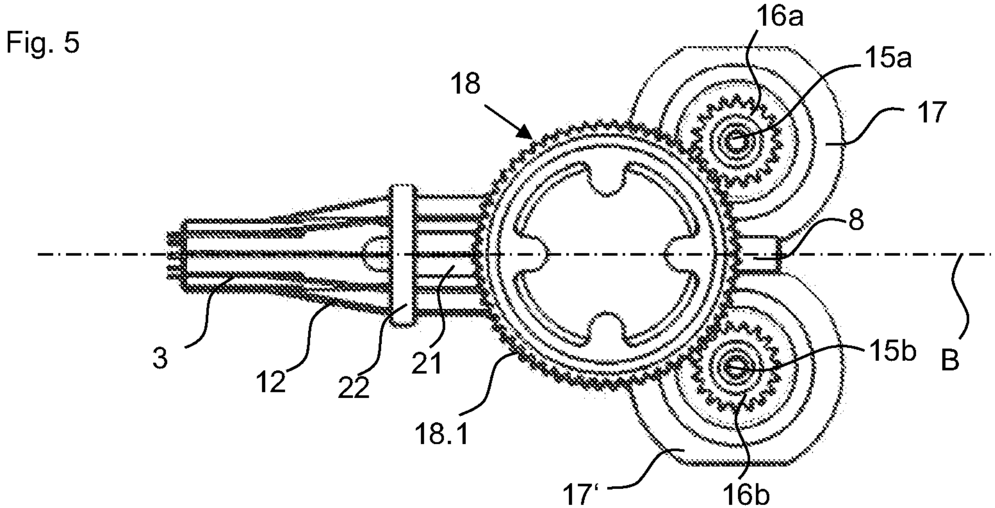
FIG. 5 shows a plan view of a variant of the drive according to FIG. 2.
Figure 6:
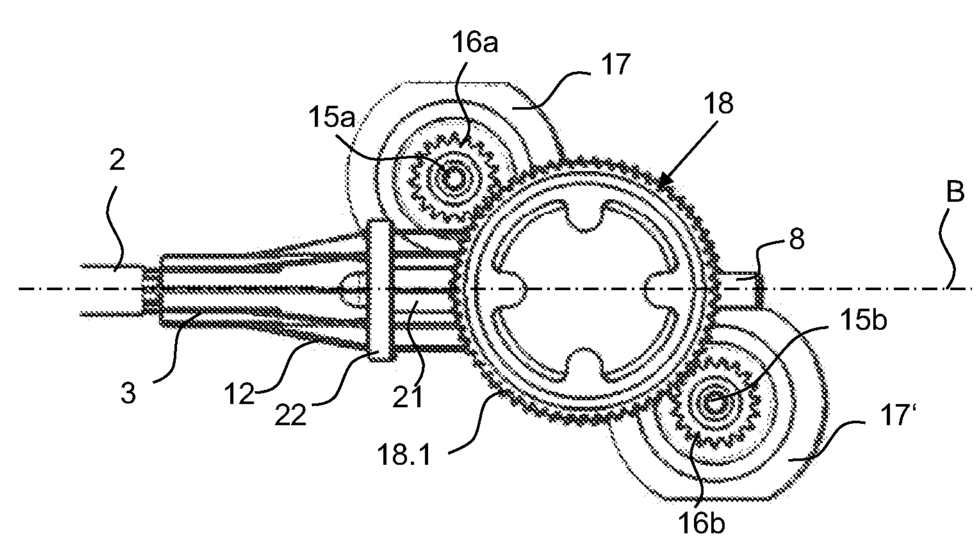
FIG. 6 shows a plan view of a further variant of the drive according to FIG. 2.

In this case, the positioning of the drive axes C, C' on a circular trajectory $U_C$ around the drive wheels 18, 19 is able to be chosen virtually without any restrictions, as indicated in FIGS. 4-6, provided the installation space there is not occupied by other instrument components such as for example the main shaft 21, the steering wires 12, the fan plate 22, or the manipulation element 8. The variants shown in FIGS. 4-6 show arrangements of the drive units made of pinions 16*a*, 16*b*, drive shafts 15*a*, 15*b*, and motors 17, 17' that are as close as possible to the longitudinal axis B and preferable as they save installation space. However, an arrangement of the drive units at any desired location on the circular trajectory $U_C$ is also conceivable, for as long as the pinions 16*a*, 16*b* mesh with the drive rims 18.1, 19.1. The diameter of the circular trajectory $U_C$ depends on the diameter of the drive wheels 18, 19 and on the diameter of the pinions 16*a*, 16*b* or toothing. Thus, a modified circular trajectory diameter which specifies the possible positioning of the drive axes C, C' may arise by changing the gear ratio.

Figures 7, 8:
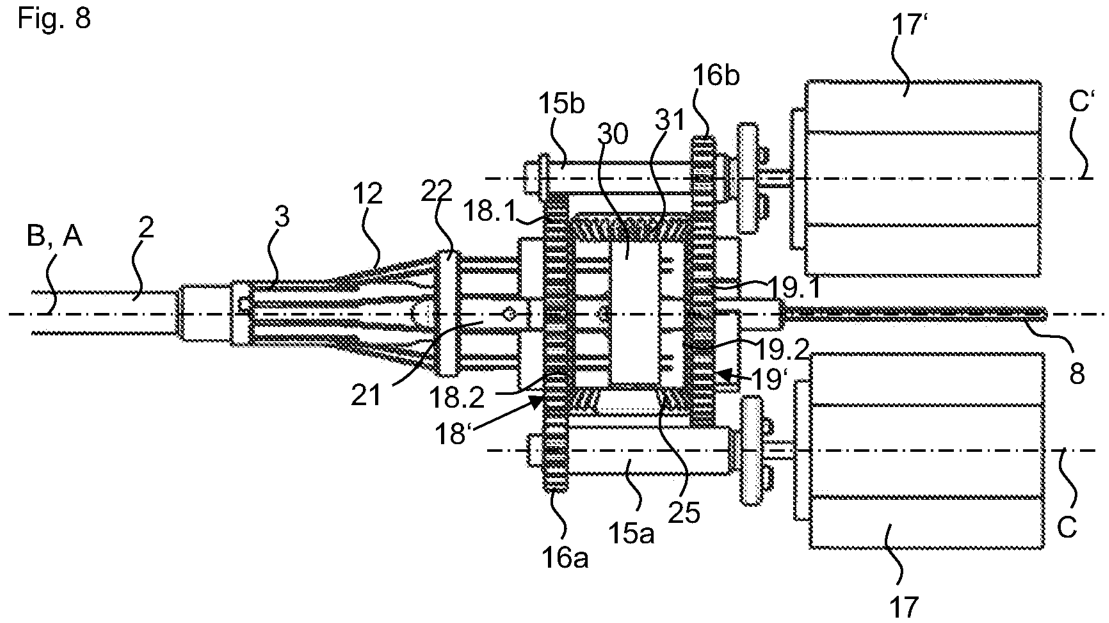
FIG. 7 shows a perspective view of the drive according to FIG. 1 in a second embodiment.
FIG. 8 shows a plan view of the drive according to FIG. 7.

FIGS. 7 and 8 illustrate an example of an alternative embodiment of the steering gear 13, in which the two drive axes C, C', which are defined by the drive units made of motor 17, 17', drive shaft 15*a*, 15*b*, and pinion 16*a*, 16*b*, run parallel to the longitudinal axis B of the surgical instrument 1. This is made possible by virtue of the double wheels driven by the drive units being designed as a hollow double wheels 18', 19', and hence being able to be arranged in the steering gear 13 in such a manner relative to the wobble plate 14 that the common axis of rotation A of the two hollow double wheels 18', 19' is flush with the longitudinal axis B of the surgical instrument 1. By hollowing out the double wheels 18', 19', the instrument components leading to the wobble plate 14, for example the main shaft 21 and steering wires 12, can be led through the double wheels 18', 19'. This also enables an installation space-saving positioning of the drive units near the longitudinal axis, wherein a positioning of the drive axes C, C' on a circular trajectory around the double wheels 18', 19' (corresponding to $U_C$ in FIG. 4) may in this case also be chosen as desired as a matter of principle.

In the examples shown in FIGS. 2 to 8, the drive rims 18.1, 19.1 of the double wheels 18, 19 or hollow double wheels 18', 19' are designed as gear rims and the pinions 16*a*, 16*b* are accordingly designed as gear wheels which engage or mesh with the drive rims 18.1, 19.1 designed as gear rims. By contrast, FIG. 9 shows an example of a further alternative embodiment of the steering gear 13 with a belt gearing for transmitting the adjustment movement of the motor 17, 17' to the respective drive wheel 18, 19.

Figure 9:
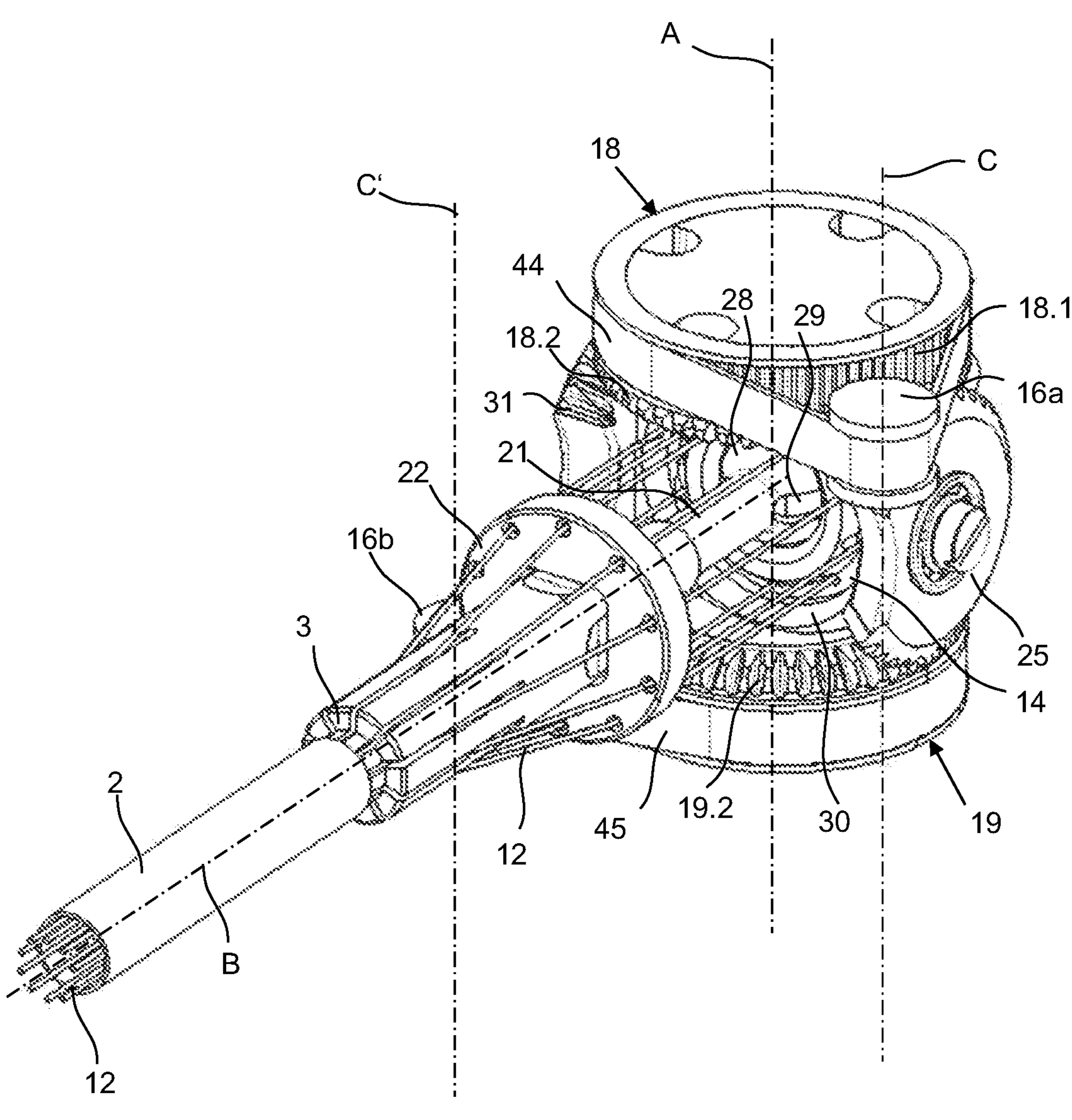
FIG. 9 shows a perspective view of the drive according to FIG. 1 in a third embodiment.

In FIG. 9, the motors have not been depicted for reasons of a better overview; however, it is self-evident that the depicted pinions 16*a*, 16*b*, designed as pulleys, are driven by a respective motor with a respective drive shaft located on the drive axes C, C'. The drive rims 18.1, 19.1 of the double wheels 18, 19 are also designed as pulleys, with the result that an adjustment movement can be transmitted from the first pinion 16*a* to the first drive wheel 18 via a first drive belt 44, and an adjustment movement can accordingly be transmitted from the second pinion 16*b* to the second drive wheel 19 via a second drive belt 45.

As evident in FIG. 9 from the drive rim 18.1, which has toothing, the belt 44 is embodied as a toothed belt in this example. Consequently, the pinion 16*a* designed as a pulley also has a toothing. A corresponding statement applies to the second drive unit, which is to say pinion 16*b*, belt 45, and drive rim 19.1, even if this is not evident from the figure.

Naturally, belt gearings deviating from a toothed belt gearing are usable, for example flat belts, round belts, V-belts, or ribbed V-belts, wherein the pulleys are formed with a circumferential profile corresponding to the drive belt. In a manner analogous to the example with the belt gearing shown in FIG. 9, an embodiment with a chain gearing is also conceivable (not depicted in the drawings), in which chains are used rather than the belts 44, 45 shown in FIG. 9 and the pinions 16*a*, 16*b* and the drive rims 18.1, 19.1 are accordingly designed as sprockets.

What emerges in the embodiments with drive belts or a corresponding drive chain is that the positioning of the pinions 16*a*, 16*b* or the drive axes C, C' can be chosen not only independently of one another and as desired on a circular trajectory around the drive wheels 18, 19 but also at any desired distance from the drive wheels 18, 19 by virtue of varying the length of the drive belt or the chain. However, since an installation space reduction is desirable, a positioning of the drive axes C, C' close to the drive wheels 18, 19, and by preference also close to the longitudinal axis B, is preferable.

The structure of the spatially adjustable plate 14 and its mount described hereinafter are identical in all embodiments of the motorized drive or steering gear 13. The structure and operation of the steering gear 13 and in particular the wobble plate 14 that is manipulable by the drive units are described below on the basis of FIGS. 3, 8, 9 and in particular FIG. 10, in which, for a better overview, only the bevel gears with the bevel gear rims 18.2, 19.2 of the drive wheels 18, 19 are depicted.

As is evident from the drawings, a hollow main shaft 21 which extends coaxially with the longitudinal axis B of the shaft 2, which is rotatable about the longitudinal axis B of the shaft 2, and which extends beyond the proximal end 3 of the shaft 2 into the region of the steering gear 13 is arranged in the shaft 2. The manipulation element 8 for manipulating the instrument 7 is axially displaceably mounted within this hollow main shaft 21.

The steering wires 12 emerging from the shaft 2 at the proximal end 3 of the shaft 2, for the purposes of which a shaft end piece 3 in which passage slots for the steering wires 12 are provided can be provided at the proximal shaft end, are fanned open in the depicted example by way of a fan plate 22 arranged for conjoint rotation with the main shaft 21 on the shaft end piece 3, thereby increasing the radial distance of the steering wires 12 from the longitudinal axis B of the shaft 2. While the diameter of the bundle of steering wires 12, which coaxially surround the longitudinal axis B of the shaft 2, is for example 4 mm within the shaft 2 or at the distal end 5 in the region of the deflection mechanism 9, the diameter of the bundle formed by the steering wires 12 is for example 18 mm behind the fan plate 22. The increase in the radial distance of the steering wires 12 from the longitudinal axis B of the shaft 2 obtained with the aid of the fan plate 22 not only simplifies the assembly and fabrication of the gear 13 equipped with the wobble plate 14 but also proportionally reduces the adjustment angle of the wobble plate 14 required for obtaining a desirably large pivot angle of the tool tip 6. With this exemplary increase in the diameter of the steering wire bundle from 4 mm within the shaft 2 to 18 mm behind the fan plate 22, an adjustment angle of the wobble plate 14 accordingly reduces 4.5-fold vis-à-vis the pivot angle of the tool tip 6 obtainable at the distal end. Thus, a pivot of the wobble plate 14 through only 200 is required to deflect said tool tip through 90°.

On the proximal side behind the fan plate 22, the steering wires 12 running parallel to the longitudinal axis B of the shaft 2 are guided to the wobble plate 14. To secure the steering wires 12 on the wobble plate 14, drilled through holes 23 are formed in the wobble plate 14 for each steering wire 12, with the steering wires 12 in the example shown being frictionally connected and affixed to the wobble plate 14 within the drilled through holes 23 by way of setscrews 24. For example, alternative forms of fastening the steering wires to the wobble plate also comprise welding or crimping or other clamping devices.

The drive wheels 18 and 19 are coupled to a third gear wheel 25 which by preference is in the form of a bevel gear and which meshes with the two bevel gear rims 18.2, 19.2 of the double wheels 18 and 19, with the result that the axis of rotation D of the third gear wheel 25 intersects the common axis of rotation A of the drive wheels 18 and 19 and the longitudinal axis B of the shaft 2. As a result of the three meshing gear wheels 18, 19 and 25, every movement of the two drive wheels 18 and 19 is directly transmitted to the wobble plate 14 that is coupled to the third gear wheel 25, bringing about a direct actuation of the steering wires 12.

Figure 10:
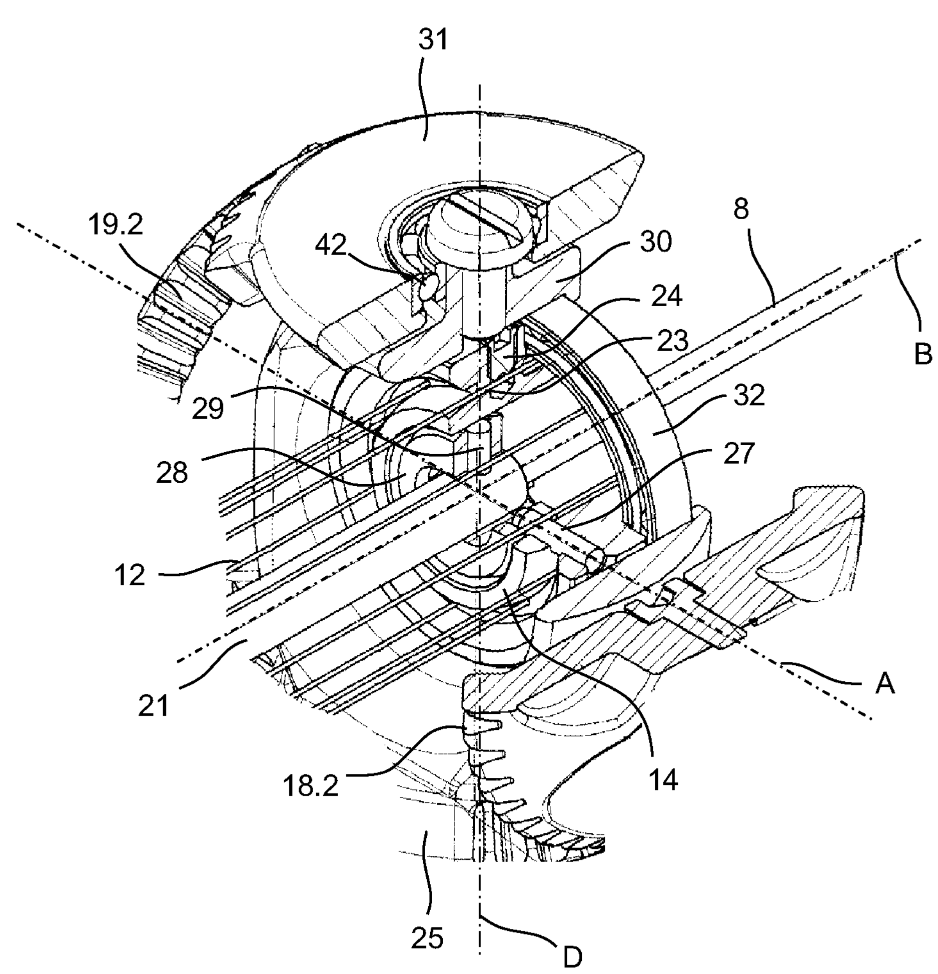
FIG. 10 shows a perspective, partly cut detailed illustration of the wobble plate gear.

To form a gimbal mount of the wobble plate 14 on the main shaft 21, the wobble plate 14 is pivotably mounted on a universal joint plate 28 by way of two bearing pins 27 arranged offset from one another by 180°, said universal joint plate in turn being pivotably mounted on the main shaft 21 by way of two bearing pins 29 arranged offset from one another by 180°. In FIG. 10, only one bearing pin 27 and one bearing pin 29 can be seen in each case on account of the partial sectional view.

In this case, the bearing pins 27 of the wobble plate 14 and the bearing pins 29 of the universal joint plate 28 are arranged offset from one another by 90°. This mount allows the wobble plate 14 to be pivoted relative to the longitudinal axis B of the shaft 2 about two axes at right angles to one another and allows a rotation of the main shaft 21 about the longitudinal axis B to be transmitted to the wobble plate 14, whereby, by way of the steering wires 12, the tool tip 6 is pivotable in all spatial directions relative to the longitudinal axis B of the shaft 2 on the distal side.

An alternative gimbal mount, not depicted here, of the wobble plate 14 on the main shaft 21 provides for the main shaft 21 to comprise, in the region provided for mounting the wobble plate 14, two guide grooves which extend along the main shaft 21, are introduced into the main shaft 21 on both sides or diametrically, and in which two diametrically and radially inwardly pointing pins which are arranged on the wobble plate 14 engage. As a result of this engagement, the wobble plate 14 can be pivoted about both the axis of rotation D and the axis of rotation A from a neutral position, in which the wobble plate 14 is located in a plane which is defined by the axis of rotation A and perpendicular, which is to say at right angles, to the longitudinal axis B. Overlaid movements as a result of pivoting about both axes of rotation A, D are likewise possible. Further, the engagement of the pins 29 in the guide grooves 20*a* enables the transfer of a rotary angle of the main shaft 21 to the wobble plate 14, with the result that the wobble plate 14 can be displaced three-dimensionally relative to the longitudinal axis B of the shaft 2. The maximum tilt or twist or the maximum tilt and rotary angles about the axes of rotation A and D are determined by the length and depth of the guide grooves 20*a* in conjunction with the internal diameter and thickness of the wobble plate 14 and length of the pins 29. In the depicted example, the main shaft 21 comprises a spherical portion 20*b* in the region provided for mounting the wobble plate 14, the guide grooves 20*a* being present in said spherical portion and the latter securing the wobble plate 14 in the axial direction. In this case, the wobble plate 14 has a contoured accommodation recess matched to the spherical portion 20*b*.

As is also evident from FIGS. 3, 8, 9 and 10, the spatially adjustable plate 14 is mounted in a steering ring 30 that is coupled for conjoint rotation with the third gear wheel 25.

To close the toothing chain formed by the drive wheels 18, 19 and gear wheel 25 to form a closed toothing ring which ensures a uniformly all-round force distribution, a fourth gear wheel 31, which is likewise by preference designed as a bevel gear and meshes with the bevel gear rims 18.2, 19.2 of the two double wheels 18 and 19, is arranged on the axis of rotation D of the third gear wheel 25 opposite to the third gear wheel 25.

By way of a bearing ring 32, the wobble plate 14 is mounted in the steering ring 30 which is coupled for conjoint rotation with the third gear wheel 25, in order to allow a rotation of the wobble plate 14 about the longitudinal axis B of the shaft 2. The steering ring 30 coupled for conjoint rotation with the third gear wheel 25 is freely rotatable in relation to the fourth gear wheel 31 as a result of mounting by means of the bearing ring 42, with the result that a rotation of the fourth gear wheel 31 about its axis of rotation D does not bring about a twist of the steering ring 30 and the wobble plate 14.

The described gimbal mount of the wobble plate 14 on the main shaft 21 allows the wobble plate 14 to be displaced three-dimensionally relative to the longitudinal axis B of the shaft 2. If, proceeding from the neutral initial position depicted in FIG. 10, in which the wobble plate 14 is aligned perpendicular to the longitudinal axis B of the shaft 2, the drive wheels 18 and 19 are driven by way of the motors 17, 17' (cf. FIGS. 2-8) such that the drive wheels 18 and 19 rotate in the same direction, this twisting of the drive wheels 18 and 19, on account of the meshing engagement with the third gear wheel 25 and the fourth gear wheel 31, brings about a tilting of the assembly, formed by the third gear wheel 25, the wobble plate 14 coupled to the third gear wheel 25, and the fourth gear wheel 31, about the common axis of rotation A of the drive wheels 18 and 19. To simplify the functional description, reference is made below to the alignment of the bearing pins 27, 29 of the gimbal mount in relation to the axes of rotation A and D. In fact, the bearing pins 27, 29 will no longer be flush with axes A and D as illustrated in the case of a rotation of the main shaft 21 and hence a rotation of the wobble plate 14, with the result that the pivot axes of the wobble plate 14 provided by the bearing pins 27, 29 may deviate from the axes of rotation A, D of the steering gear 13.

This tilt of the wobble plate 14 relative to the main shaft 21 is enabled by the bearing pins 27, which are flush with the axis of rotation A of the drive wheels 18 and 19 and by means of which the wobble plate 14 is pivotably mounted on the universal joint plate 28. This tilt of the wobble plate 14 about the axis of rotation A relative to the longitudinal axis B of the shaft 2 brings about, distally and by way of the steering wires 12, a corresponding pivot of the tool tip 6 relative to the longitudinal axis B of the shaft 2.

If, proceeding from the neutral initial position depicted in FIG. 10, in which the wobble plate 14 is aligned perpendicular to the longitudinal axis B of the shaft 2, the drive wheels 18 and 19 are driven by way of the motors 17, 17' such that the drive wheels 18 and 19 rotate in opposite directions, this twisting of the drive wheels 18 and 19, on account of the meshing engagement with the third gear wheel 25, brings about a twisting of the assembly, formed by the third gear wheel 25 and the wobble plate 14 coupled to the third gear wheel 25, about the axis of rotation D of the third gear wheel 25.

This twist of the universal joint plate 28 relative to the main shaft 21 is enabled by the bearing pins 29, which are flush with the axis of rotation D of the third gear wheel 25 and by means of which the universal joint plate 28 is pivotably mounted on the main shaft 21, together with the free rotatability of the wobble plate 14 relative to the fourth gear wheel 31 on account of the bearing ring 32. This twist of the wobble plate 14 about the axis of rotation D relative to the longitudinal axis B of the shaft 2 brings about, distally and by way of the steering wires 12, a corresponding pivot of the tool tip 6 relative to the longitudinal axis B of the shaft 2.

Further, it is naturally possible to overlay the movements described, with the result that, for example, the wobble plate 14 is tilted about the common axis of rotation A of the drive wheels 18, 19 and, at the same time, is also additionally twisted about the axis of rotation D of the third gear wheel 25. As a result of combining the two sequences of motion on account of the individually controllable motors 17, 17' of the gear 13 and the coupling with the main shaft 21, it is possible to three-dimensionally adjust the wobble plate 14 relative to the longitudinal axis B of the shaft 2, from which a corresponding spatial displacement of the tool tip 6 results on account of the coupling via the steering wires 12.

A surgical instrument 1 embodied as described above is distinguished in that many thin steering wires 12 can be used to control the pivotable tool tip 6 and that, on account of the motorized drive 13 for the wobble plate 14 on which the steering wires 12 are mounted, this control is sensitive, precise and reproducible.

An exemplary embodiment of the disclosure is depicted in the drawings. The drawings, the description, and the claims contain numerous features in combination. A person skilled in the art will expediently also consider the features on an individual basis and combine them to form further advantageous combinations. The present disclosure provides a steering gear 13 for a surgical instrument 1, arrangeable at the proximal end 3 of a shaft 2 which defines a longitudinal axis B and has a deflection mechanism 9 at the distal end 5, wherein the steering gear 13 has two motorized drives and is designed to spatially orient a wobble plate 14 by way of the adjustment angles of the two drives. The two drives each comprise a drive wheel 18, 18', 19, 19' which is driven by motors 17, 17' and designed as a double wheel 18, 18', 19, 19' with a bevel gear rim 18.2, 19.2 and a drive rim 18.1, 19.1. Here, the wobble plate 14 is arranged between the two drive wheels 18, 19; 18', 19', which have a common axis of rotation A, and the bevel gear rims 18.2, 19.2 are arranged facing one another, wherein the drive rims 18.1, 19.1 of both double wheels 18, 19; 18', 19' are operatively connected to a respective pinion 16*a*, 16*b*. Here, the pinions 16*a*, 16*b* which are each operatively connected to one of the drive rims 18.1, 19.1 are drivable by the respective motor 17, 17' via a respective drive shaft 15*a*, 15*b*, which defines a drive axis C, C', wherein the two drive axes C, C' run parallel to one another and parallel to the common axis of rotation A of the two drive wheels 18, 19; 18', 19'. Furthermore, a surgical instrument 1 is disclosed which comprises such a steering gear 13.

The invention claimed is:

1. A steering gear for a surgical instrument, arrangeable at the proximal end of a shaft defining a longitudinal axis and has a deflection mechanism at the distal end, wherein the steering gear comprises:

two motorized drives and is designed to spatially orient a wobble plate by way of an adjustment angle of the two motorized drives, the wobble plate is designed to control the distal deflection mechanism of the surgical instrument, wherein the two motorized drives include a first drive and a second drive, the first drive includes a first drive wheel that is driven by a first motor and designed as a double wheel with a first bevel gear rim and a first drive rim, and the second drive includes a second drive wheel that is driven by a second motor and designed as a double wheel with a second bevel gear rim and a second drive rim, wherein the wobble plate is arranged between the two drive wheels, the two drive wheels have a common axis of rotation, and the bevel gear rims are arranged facing one another, and wherein the first drive rim and the second drive rim of the corresponding first drive wheel and the second drive wheel are operatively connected to a respective first pinion and a second pinion, respectively, wherein the first pinion that is operatively connected to the first drive rim is drivable by the first motor via a first drive shaft, the first drive shaft defining a first drive axis, and the second pinion that is operatively connected to the second drive rim is drivable by the second motor via a second drive shaft, the second drive shaft defining a second drive axis, and wherein the two drive axes run parallel to one another and parallel to the common axis of rotation of the two drive wheels.

2. The steering gear as set forth in claim 1, wherein the two double wheels of the steering gear are arranged relative to the wobble plate in such a way that the two drive axes and the common axis of rotation of the two double wheels run perpendicular to the longitudinal axis of the surgical instrument, wherein the motors are arranged next to one another on one side in relation to the longitudinal axis.

3. The steering gear as set forth in claim 1, wherein the first drive wheel is designed as a hollow double wheel and the second drive wheel is designed as a hollow double wheel, and the two hollow double wheels of the steering gear are arranged relative to the wobble plate in such a way that the common axis of rotation of the two hollow double wheels is flush with the longitudinal axis of the surgical instrument, and the two drive axes run parallel to the longitudinal axis of the surgical instrument.

4. The steering gear as set forth in claim 1, wherein the first drive rim and the second drive rim are gear rims, and the first pinion and the second pinion are gear wheels which that mesh with a corresponding one of the first drive rim and the second drive rim.

5. The steering gear as set forth in claim 1, wherein the first drive rim, the second drive rim, the first pinion and the second pinion are pulleys configured to engage a first drive belt and a second drive belt, wherein the first drive belt provides the operative connection between the first drive rim and the first pinion and the second drive belt provides the operative connection between the second drive rim and the second pinion.

6. The steering gear as set forth in claim 5, wherein each drive belt is a flat belt, round belt, V-belt, ribbed V-belt, or toothed belt, and the all-round profile of the first drive rim, the second drive rim and the first pinion and the second pinion accordingly is a flat profile, round profile, V-profile, ribbed V-profile or toothed profile.

7. The steering gear as set forth in claim 1, wherein the wobble plate is coupled to a third gearwheel that meshes with the two bevel gear rims of the two double wheels and an axis of rotation of the third gear wheel is at right angles to the common axis of the double wheels, wherein the wobble plate is coupled to a fourth gear wheel that is coupled to the two bevel gear rims of the two double wheels and arranged on the side facing away from the third gear wheel.

8. A surgical instrument comprising:

a shaft a manipulation unit arranged at the proximal end of the shaft, and an instrument arranged at the distal end of the shaft with a tool tip, wherein the tool tip is configured to be deflected by means of a distal deflection mechanism and the tool tip is configured to be controlled by the wobble plate that can be spatially oriented by means of two drives, characterized in that the surgical instrument comprises:

the steering gear as set forth in claim 1, being designed to transfer the adjustment angle of the two motorized drives to the spatial alignment of the wobble plate.

9. The surgical instrument as set forth in claim 8, characterized in that for the purpose of coupling with a third gear wheel that meshes with the two bevel gear rims of the two double wheels, the wobble plate, via a bearing ring, is mounted so as to be rotatable about the longitudinal axis of the shaft in a steering ring that is coupled for conjoint rotation with the third gear wheel, the wobble plate being coupled to a main shaft running coaxially with a longitudinal axis of the shaft so as to move in three degrees of freedom.

10. The surgical instrument as set forth in claim 9, characterized in that the wobble plate is pivotably mounted on a universal joint plate by way of two bearing pins arranged offset from one another by 180°, wherein the universal joint plate is pivotably mounted on the main shaft by way of two bearing pins arranged offset from one another by 180°, and wherein the bearing pins of the wobble plate and the universal joint plate are arranged offset from one another by 90°, or pivotably mounted by two longitudinally extending guide grooves diametrically present in the main shaft and two diametrically and radially inwardly pointing pins arranged on the wobble plate, wherein each pin engages in one of the guide grooves such that a rotary angle of the main shaft is transferable to the wobble plate.

11. The surgical instrument as set forth in claim 8, wherein a plurality of steering wires are connected to the wobble plate of the steering gear run in the longitudinal direction of the shaft.

12. The surgical instrument as set forth in claim 11, characterized in that a fourth gear wheel is coupled to the wobble plate via a bearing ring with a steering ring, wherein the fourth gear wheel freely rotatable vis-A-vis a third gear wheel.

13. The surgical instrument as set forth in claim 11, further including a manipulation element that is axially displaceably mounted in the shaft and is operatively connected to the manipulation unit on the proximal side, wherein the distal deflection mechanism consists of pivot members that are arranged at the distal end of the shaft and connected to the steering gear by way of steering wires running in the longitudinal direction of the shaft.

14. The surgical instrument as set forth in claim 11, wherein a radial distance of the steering wires from the longitudinal axis of the shaft at the wobble plate is greater than the radial distance of the steering wires from the longitudinal axis of the shaft at the proximal end of the shaft, wherein—the steering wires extend directly to the wobble plate from the proximal end of the shaft, with the steering wires running at an angle with respect to the wobble plate that deviates from 90°, or a fan plate is arranged on the main shaft and on a distal side of the wobble plate, the distal side opposite of the first and second drive wheels, said fan plate fixing the radial distance of the steering wires from the longitudinal axis of the shaft so as to place the steering wires in parallel to one another and the shaft between the fan plate and the wobble plate and, in relation to a plate surface of the wobble plate, form an angle of 90°.

15. The steering gear as set forth in claim 1, wherein the first drive rim, the second drive rim, the first pinion and the second pinion are designed as sprockets for a first drive chain and a second drive chain, wherein the first drive chain provides the operative connection between the first drive rim and the first pinion; and the second drive chain provides the operative connection between the second drive rim and the second pinion.

* * * * *